United States Patent [19]
Takahashi

[11] Patent Number: 6,094,595
[45] Date of Patent: Jul. 25, 2000

[54] COSMETIC DEVICE

[76] Inventor: Kohno Takahashi, 17-8, Chuoh-cho, Isezaki-city, Guma, 372-0042, Japan

[21] Appl. No.: 09/216,438

[22] Filed: Dec. 18, 1998

[30] Foreign Application Priority Data

May 22, 1998 [JP] Japan .................................. 10-141664

[51] Int. Cl.$^7$ ................ A61N 1/06; A61N 5/06
[52] U.S. Cl. ................ 607/3; 607/88; 607/115; 607/150
[58] Field of Search ................ 606/9, 41, 32, 606/10, 11, 13, 34; 607/88, 3, 1, 50, 115, 145, 150, 184; 128/907

[56] References Cited

U.S. PATENT DOCUMENTS 4,930,504  6/1990  Diamantopoulos et al. .............. 607/88
5,908,444  6/1999  Azure ........................................ 607/88

FOREIGN PATENT DOCUMENTS 7-352     1/1995  Japan .
9-276354  10/1997 Japan .
10-57441  3/1998  Japan .

Primary Examiner—Lee Cohen
Assistant Examiner—B. Nicholas Guy
Attorney, Agent, or Firm—Frishauf, Holtz, Goodman, Langer & Chick, P.C.

[57] ABSTRACT

A cosmetic device is provided with: a light beam generating part; a light beam probe for outputting therethrough a light beam from the light beam generating part; a high-potential pulse generating part; a needle pulse probe and a spherical pulse probe for outputting therethrough high-potential pulses from the high-potential pulse generating part; a control part for controlling the intensity, output time and output interval of each of the light beam from of the light beam probe and the pulse from said needle or spherical pulse probe; and a display part for displaying the state of control by the control part and the state of operation of the cosmetic device. The light beam probe is a halogen lamp and the spherical pulse probe is a gas-filled lamp.

10 Claims, 5 Drawing Sheets

GAS FOR DISCHARGE

COSMETIC DEVICE

BACKGROUND OF THE INVENTION

The present invention relates to a cosmetic device with which it is possible to remove skin wastes and blemishes such as blotches, freckles, moles, warts and hemorrhoids.

Heretofore, people have had skin wastes and blemishes removed by surgical operations or irradiation with laser light in specialized hospitals.

However, such treatment incurs expenses, takes much time, and sometimes leaves scars on the skin.

SUMMARY OF THE INVENTION

It is therefore an object of the present invention to provide a cosmetic device which permits easy removal of skin wastes and blemishes in a beauty shop or at home.

According to an aspect of the present invention, there is provided a cosmetic device which comprises: a light beam generating part; a light beam probe for outputting therethrough a light beam from the light beam generating part; a high-potential pulse generating part; a needle pulse probe and a spherical pulse probe for outputting therethrough high-potential pulses from the high-potential pulse generating part; a control part for controlling the intensity, output time and output interval of each of the light beam from the light beam probe and the pulse from the needle or spherical pulse probe; and a display part for displaying the state of control by the control part and the state of operation of the cosmetic device.

According to another aspect of the present invention, the light beam probe is a halogen lamp.

According to still another aspect of the present invention, the spherical pulse probe is a gas-filled lamp.

Other objects, features and advantages of the present invention will become more apparent from the following detailed description taken in conjunction with the accompanying drawings.

DESCRIPTION OF THE PREFERRED EMBODIMENT

To facilitate a better understanding of the present invention, a brief description will be given first of findings on which the invention is based.

It is well-known in the art that ozone ($O_3$) has a strong oxidizing action and possesses the property of absorbing infrared rays as well as bleaching, sterilizing and anti-inflammatory properties. Further, the ozone has such properties as listed below, and is utilized in various fields.

1. When changing to oxygen in the air, ozone takes on sterilizing properties and kills bacteria and toxins on the skin surface without damaging healthy skin tissue. This property has already used to treat wounds, for instance.

2. The oxidizing property that ozone takes on when changing to oxygen in the air (ozone itself is reduced) has also been used to sterilize drinking water, dean air and preserve food.

3. Lotion, cream and the like, if applied together with ozone, are quickly absorbed into the skin.

4. By irradiating the skin with ozone, harmful substances (wastes) on the skin surface are decomposed, and at the same time, sebaceous and sweat glands are activated, making it possible to get rid of pimples, eruptions, blotches, moles, warts, hemorrhoids or similar skin blemishes from the skin surface.

It is also well-known that ozone is generated by a discharge in oxygen, and ozone generators are now in wide use. The cosmetic device of the present invention has been developed on the basis of the above findings.

A description will be given, with reference to the accompanying drawings, of the cosmetic device of the present invention.

Figure 1:
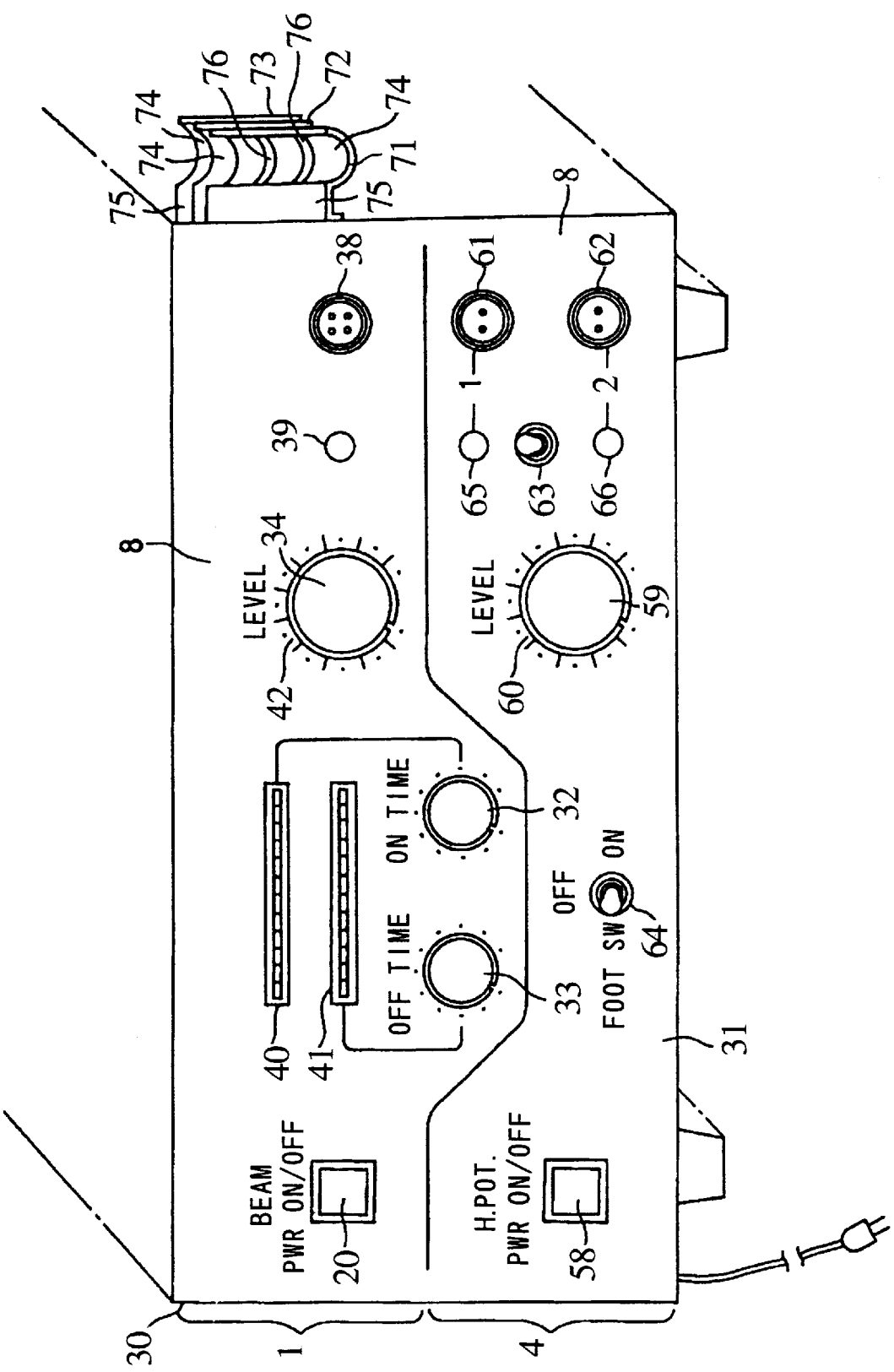
FIG. 1 is a front view of a cabinet of the cosmetic device according to the present invention.

As depicted in FIGS. 1 and 2, the cosmetic device according to an embodiment of the present invention comprises: a light beam generating part 1; a light beam probe 3 for outputting therethrough a light beam from the light beam generating part 1; a high-potential pulse generating part 4; a needle pulse probe 5 and a spherical pulse probe 6 for outputting therethrough high-potential pulses from the high-potential pulse generating part 4; a control part 7 for controlling the intensity, output time and output interval of each of the light beam from the light beam probe 3 and the pulse from the needle or spherical pulse probe 5 or 6; and a display part 8 for displaying the state of control by the control part 7 and the state of operation of the cosmetic device.

Figure 3:
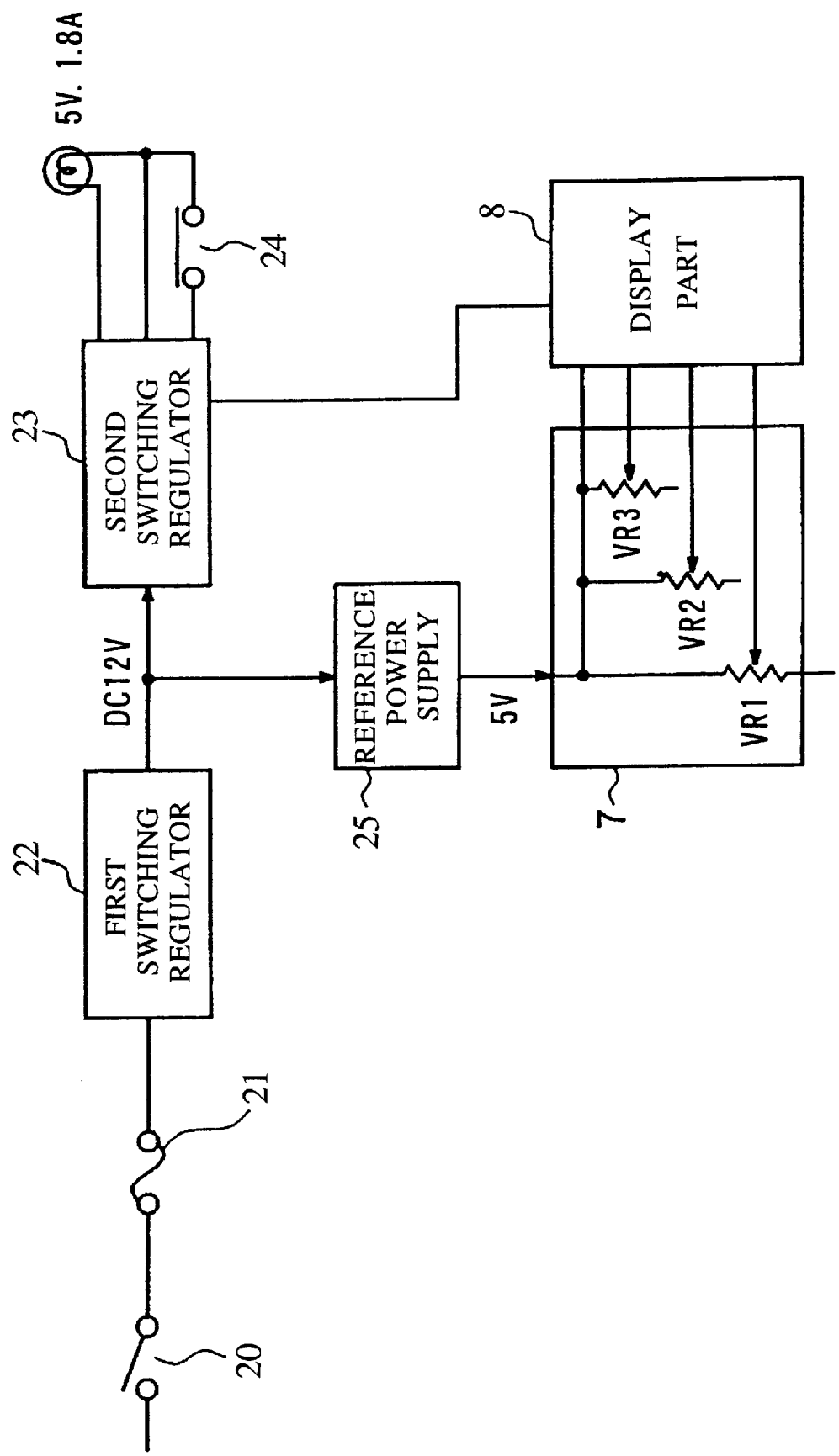
FIG. 3 is a circuit diagram for explaining a light beam generator of the cosmetic device according to the present invention.

FIG. 3 illustrates in block form the light beam generator 1, which is made up of a power switch 20, a first switching regulator 22 connected via a fuse 21 to a 100-volt commercial power supply, a second switching regulator 23, a remote switch 24, a reference power supply 25, the control part 7, and the display part 8.

The first switching regulator 22 is an AC-DC converter for converting 100-volt AC to 12-volt DC The second switching regulator 23 is to efficiently convert the 12-volt DC from the first switching regulator 22 to power necessary for the light beam probe 3, and outputs a voltage in the range of 1.5 to 5.7 volts. The reference power supply 25 is to create a stable reference voltage (for example, 5 volts) from the above-mentioned 12-volt DC. Based on the 5-volt reference voltage, the control part 7 adjusts or controls the light beam oscillation time and quiescent time of the light beam generating part 1, the output level of the light beam and the brightness of the light beam probe (halogen lamp) 3 when it is lit.

The control part 7 is provided with three variable resistors VR1, VR2 and VR3, which are used to adjust the light beam oscillation time, the light beam quiescent time and the light beam output level, respectively. The resistance values of the variable resistors VR1, VR2 and VR3 are adjusted by turning an oscillation time (ON TIME) adjustment knob 32, a light beam quiescent time (OFF TIME) adjustment knob 33 and an output level adjustment knob 34 mounted on the front panel 31 of the cabinet 30 as depicted in FIG. 1. The light beam oscillation time and the quiescent time are adjusted by turning the oscillation time adjustment knob 32 and the quiescent time adjustment knob 33, respectively, and the light beam output level is adjusted by turning the output level adjustment knob 34.

Figure 2A:
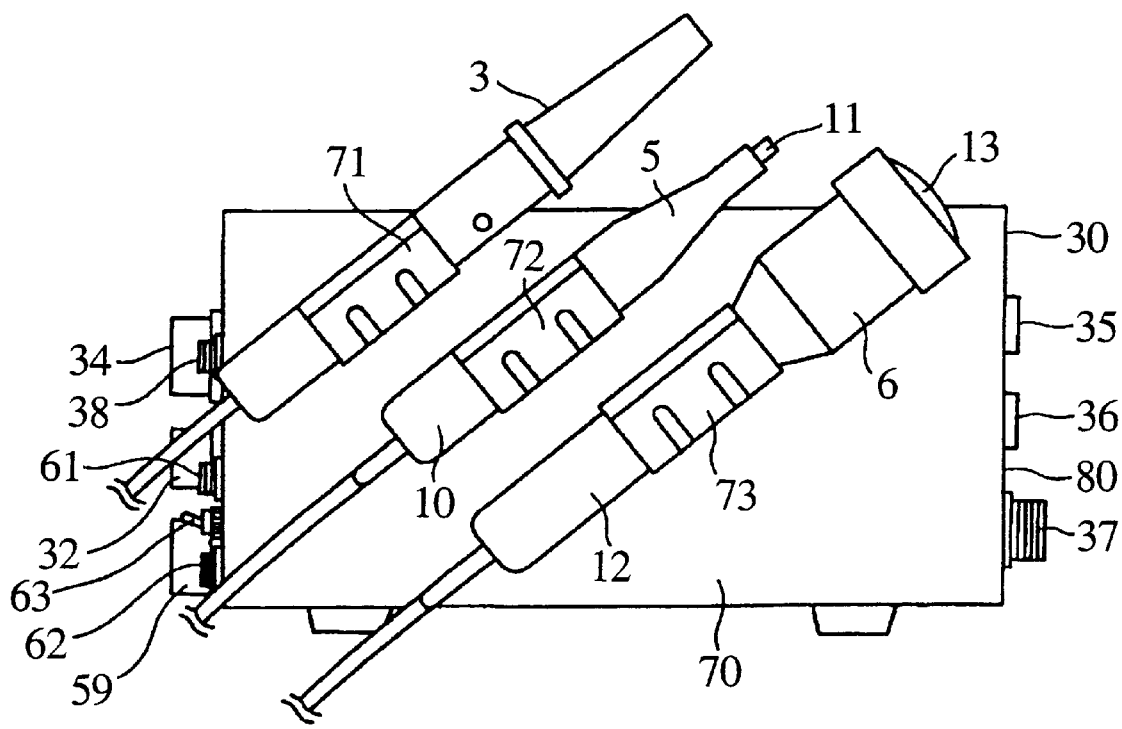
FIG. 2(a) is a side view of the cabinet depicted in FIG. 1.

The light beam probe 3 is a halogen lamp that produces a 5-volt, 1.8-ampere (9-watt) output. As depicted in FIG. 2(a), the light beam probe 3 is slender, several centimeters in diameter and ten-odd centimeters in length, and hence it can be held by one's thumb, forefinger and middle finger. The light beam probe 3 has at its tip end portion a built-in spherical lens about 4 mm in diameter so that light from the light beam generating part 1 is focused by the spherical lens into a light beam for irradiation. By irradiating the skin with the light beam from the light beam probe 3, it is possible to obtain the same effect as by moxa cautery and a depilation effect.

Figure 5:
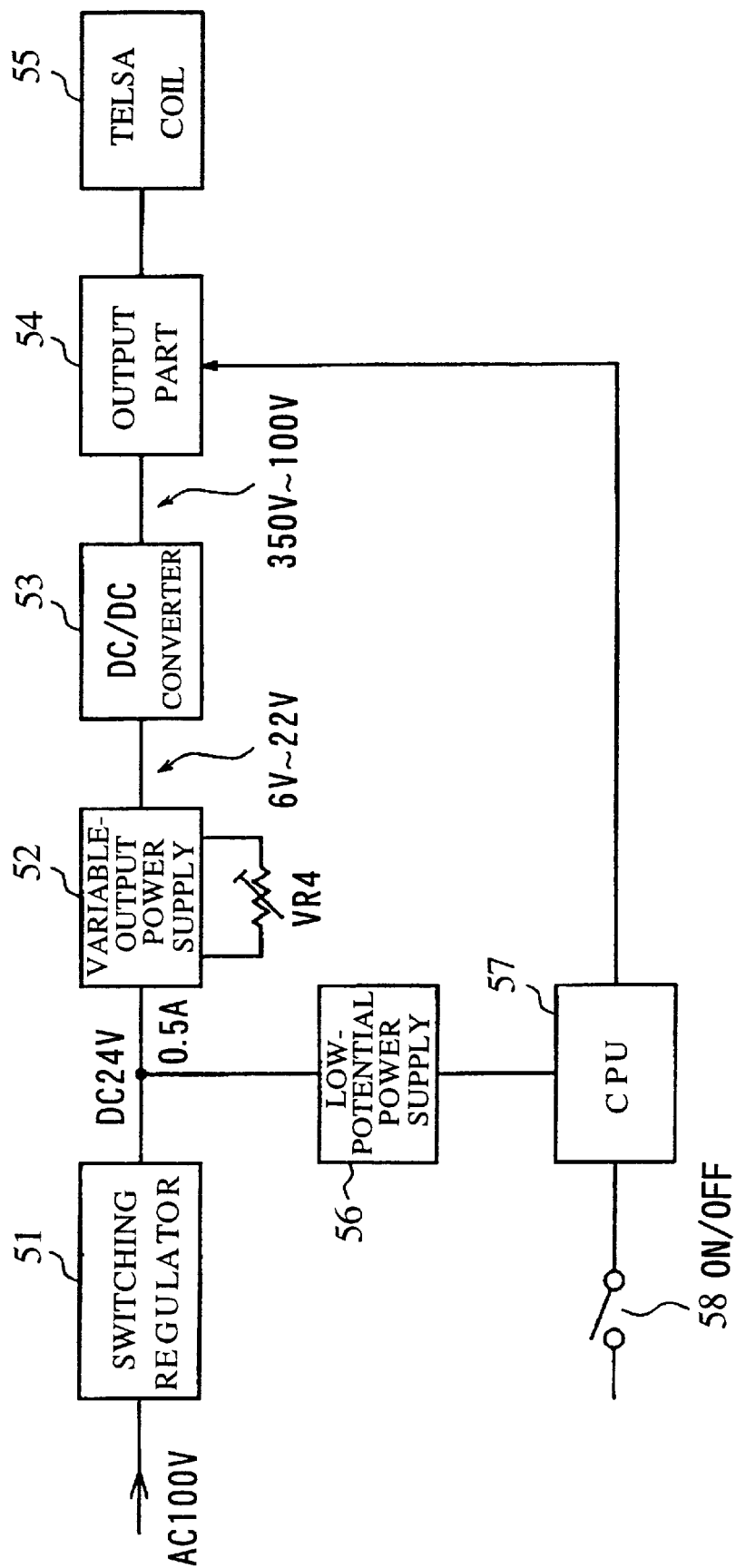
FIG. 5 is a circuit diagram for explaining a high-potential pulse generating part of the cosmetic device according to the present invention.

FIG. 5 illustrates in block form the circuit configuration of the high-potential pulse generating part 4, which is able to generate high-potential pulses from 30,000 to 40,000 volts peak-to-peak. The high-potential pulse generating part 4 depicted in FIG. 5 is made up of a switching regulator 51 which is supplied with a 100-volt AC commercial power, a variable-output power supply 52, a DC-DC converter 53, an output part 54, a Tesla coil 55, a low-potential power supply 56, a CPU 57, and a high-potential pulse power switch 58.

The switching regulator 51 is also called an AC-DC converter or switching power supply, and converts 100 volts AC to 24 volts DC, producing a 25-volt DC, 0.5-ampere output. The variable-output power supply 52 is one that is capable of changing its output level in the range of 6 to 22 volts by turning a variable resistor VR4. The variable resistor VR4 is turned through an output adjustment knob 59 depicted in FIG. 1, and its output level is indicated by calibration markings provided around the knob 59.

The DC-DC converter 53 is to convert the output voltage from the variable-output power supply 52 to a voltage in the range of from 100 to 350 volts. The output part 54 switches the output voltage from the DC-DC converter 53 at high speed and feeds it to the Tesla coil 55. The Tesla coil 55 is built in the acicular pulse probe 5, and is a coil of the type wherein a fast current feed to a primary winding creates a high voltage in the secondary winding; the coil 55 is capable of generating pulses in the range of as high as 30,000 to 40,000 volts peak-to-peak. Incidentally, the Tesla coil 55 has no capacity of drawing such a high current as to cause electrocutions.

The low-potential power supply 56 is to obtain a 5-volt power necessary for actuating the CPU 57, and is adapted to derive 5-volt DC from the output voltage (24-volt DC) of the switching regulator 51.

The CPU 57 activates the output part 54 when the high-potential pulse power switch 58 is in the ON state. If the power switch 58 is left remaining ON, the output from the output part 54 also remains ON for a long time accordingly. To avoid this, the power switch 58 is so designed so to automatically turn OFF after a lapse of a fixed ON-state period, stopping the output from the output part 54. Turning ON the power switch 58 after once turning it OFF, the output part 54 resumes its operation.

The high-potential pulses from the high-potential pulse generating part 4 are discharged to the outside through the needle or spherical pulse probe 5 or 6. As depicted in FIG. 2(a), the needle pulse probe 5 has a needle discharge electrode 11 mounted at the tip of a slender grip 10 which is several centimeters in diameter and ten-odd centimeters in length and hence can be held by one's thumb, forefinger and middle finger. The needle pulse probe 5 is adapted to discharge when the discharge electrode 11 is placed one centimeter or less apart from the skin. This discharge activates (ionizes) oxygen (O) in the air, generating ozone. Since the ozone has bleaching and sterilizing power, it is possible to remove blotches, moles, warts or similar blemishes from the skin by its irradiation with the high-potential pulses which are discharged from the electrode 11. With too thin the needle discharge electrode 11, there is a fear of its tip being melt by the heat resulting from discharge; therefore, the needle electrode 11 is so thick as not to be melt during discharge.

Figure 4:
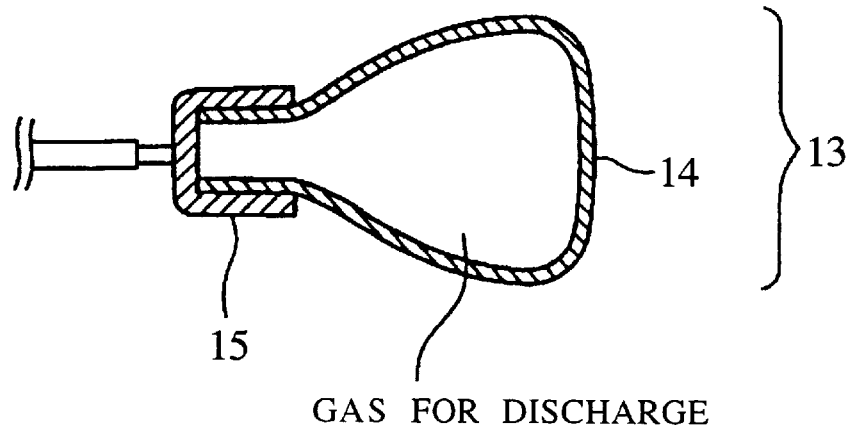
FIG. 4 is a sectional view of a discharge-type gas-filled lamp for use as a spherical pulse probe in the present invention.

The spherical pulse probe 6 has, as depicted in FIG. 2(a), a discharge type gas-filled lamp 13 attached to the tip of a slender grip 12 which is several centimeters in diameter and ten-odd centimeters in length and hence can be held by one's thumb, forefinger and middle finger. The gas-filled lamp 13 is a sphere of glass which has a somewhat flat forward end face as indicated by 14 in FIG. 4. The sphere 14 has filled therein halogen, neon (Ne), argon (Ar), nitrogen (N) or similar gas for discharge. When a high-voltage a.c. current is applied to an electrode 15 of the lamp 13, the gas filled in the sphere 14 ionizes and discharges, emitting light The color of light by the discharge varies with the gas filled in the sphere 14. Since the sphere 14 is made of glass, no charges pass therethrough when the high-potential current to the electrode 15 is d.c. current. In the present invention, however, since the high-potential current is a.c. current (high-potential pulses), charges pass through the glass sphere 14 due to electrostatic induction. When the discharge type gas-filled lamp 13 is held in contact with the skin, the above-mentioned charges flow to the skin from the lamp 13.

The light beam generating part 1, the high-potential pulse generating part 4, the power supply circuits and so forth are built in the cabinet 30 shown in FIGS. 1 and 2(a). On the back 80 of the cabinet 30 there are mounted an AC cord receptacle 35, a fuse holder 36, a foot switch connector 37 to which is detachably connected a foot switch for connection to the high-potential pulse generator.

The front panel 31 of the cabinet 30 depicted in FIG. 1 is divided into upper and lower areas. In the upper area there are mounted a beam power switch (an illuminated push-button switch) 20, the beam intensity (output level) adjustment knob 34 for adjusting the output intensity of the light beam, the ON time adjustment knob 32 for adjusting the light beam ON period, the OFF time adjustment knob 33 for adjusting the light beam OFF period, and a beam probe connector 38 which detachably receives the light beam probe 3. The display part 8 provided in the upper area of the front panel 31 includes an ON-indication lamp 39 which lights up during the light beam output time interval, a bar LED 40 as an elapsed time indicator of the light beam ON time, a bar LED 41 as an elapsed time indicator of the light beam OFF time, and level-indicating calibration markings 42 provided around the beam intensity adjustment knob 34. The bar LED 40 lights up over a length corresponding to the length of the light beam ON time, and its light-up time changes with the rotational angular position of the ON time adjustment knob 32. The bar LED 41 also lights up over a length corresponding to the length of the light beam OFF time, and its light-up time changes with the rotational angular position of the OFF time adjustment knob 33. The level-indicating calibration markings 42 indicate the rotational angular position (output level) of the output level adjustment knob 34.

In the lower area of the front panel 31 there are placed a power switch (an illuminated push-button switch) 58 for the high-potential pulse generator, a high-potential pulse output adjustment knob 59 for adjusting the high-potential pulse output, pulse probe connectors 61 and 62 for detachably connecting thereto the two pulse probes, a select switch 63 for selecting either one of the pulse probe connectors 61 and 62 to output the high-potential pulses, and a select switch 64 for connection to a foot switch connected to the foot switch connector 37 provided on the back 80 of the cabinet 30. A display part 8 for the high-potential pulse is also provided in the lower area of the front panel 31. The display part 8 includes ON-indication lamps 65 and 66 for indicating which of the pulse probe connectors 61 and 62 is being selected, and calibration markings 60 provided around the high-potential output adjustment knob 59 for indicating its rotational position (output level).

When tuned ON, the illuminated beam power switch 20 depicted in FIG. 1 illuminates, switching ON the light beam generator 1 to emit a light beam. In this instance, the beam ON time can be freely set by turning the ON time adjustment knob 32, and the beam OFF time can similarly be set at will by turning the OFF time adjustment knob 33. By this, the ratio between the beam ON and OFF durations can be set accordingly. When the both adjustment knobs 32 and 33 are set at the same value, the beam ON and OFF times are equal. When the knob 32 is set at a value larger than the knob 33, the beam ON time is longer than the OFF time; in the reverse case, the beam ON time is shorter than the OFF time. With the ON time maximized and the OFF time minimized, the light beam is continuously emitted. The ON and OFF time intervals can be set arbitrarily in accordance with the skin and other conditions. For example, the beam ON time is a few tenth of a second to several seconds and the OFF time also a few tenth of a second to several seconds. During the beam ON time the bar LED 40 stays illuminated to indicate the length of the ON time, and during the beam OFF time the bar ED 41 stays illuminated to indicate the length of the OFF time. Hence, the ratio between the ON and OFF times can be ascertained from the lengths of light-up times of the LEDs 40 and 41. The beam intensity can be adjusted by turning the adjustment knob 34.

Figure 2B:
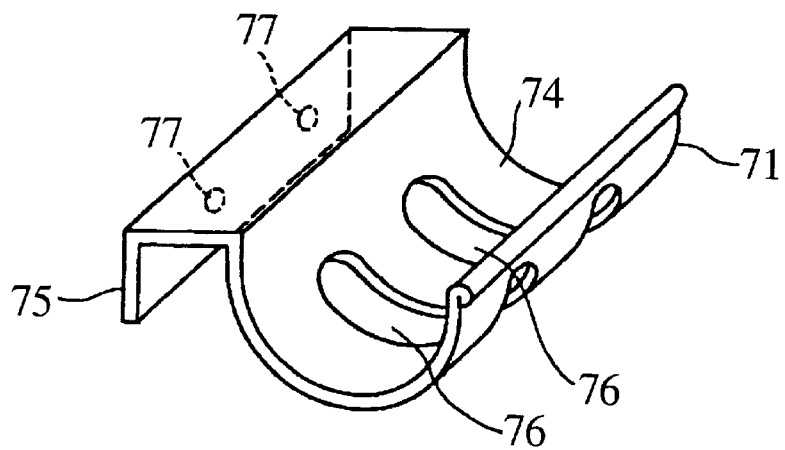
FIG. 2(b) is a perspective view of a probe holder for use in the present invention.

On one side 70 of the cabinet 30 there are mounted, as depicted in FIG. 2(a), a beam probe holder 71 for holding the light beam probe 3, a needle probe holder 72 for holding the needle probe 5 and a spherical probe holder 73 for holding the spherical probe 6. These holders 71, 72 and 73 are identical in shape. As depicted in FIGS. 2(a) and (b), each holder has a semicylindrical receiving portion 74 formed by bending a sheet of stainless steel and a flat, straight mounting portion 75 contiguous to or integral with the receiving portion 74. The seicylindrical receiving portion 74 has notches 76 cut therein, and hence it releasably grips the corresponding probe. The mounting portion 75 has through holes 77 for receiving screws as shown in FIG. 2(b). These holders are each mounted on the cabinet 30 with the mounting portion 75 fastened to the side 70 thereof by screws. The holders 71, 72 and 73 are tilted forward and displaced apart in the vertical direction so that the probes can easily be fitted therein and removed therefrom as required. In this instance, the inner diameter of the probe receiving portion 74 is somewhat smaller than the diameter of the probe so that the receiving portion 74 resiliently holds the probe forced thereinto.

While in use, the needle pulse probe 5 and the spherical pulse probe 6 are connected to the pulse probe connectors 61 and 62, respectively. The power switch 58 is held in the ON state, and either one of the needle pulse probe 5 and the spherical pulse probe 6 is selected by the select switch 63 for connection to the power supply. When the needle pulse probe S is selected, the ON-indication lamp 65 lights up, and when the spherical pulse probe 6 is selected, the ON-indication lamp 66 lights up. The output level of either pulse probes is adjusted by manually tuning the output level adjustment knob 59.

When a foot switch is used, it is connected to the foot switch connector 37 mounted on the back 80 of the cabinet 30 and the select switch 64 on the front panel 31 is turned ON. The foot switch is operated by a user's foot to adjust the high-potential pulse output.

Next, a description will be given below of how to use the cosmetic device of the present invention to take care of the skin on a daily basis.

1. Remove makeup with cleansing cream.
2. Wash face with soap, fadal cleansing foam, or the like.
3. Spread cream on face and apply a face massage for two minutes or so by holding the discharge type gas-filled lamp 13 of the spherical pulse probe 6 directly against the skin. Slight vibration by discharge facilitates cleaning the skin and stimulates blood circulation. At this time, the skin is cleaned by the sterilizing, bleaching and anti-inflammatory properties of ozone generated by the discharge from the gas-filled lamp 13.
4. Wipe off the massage cream and wash face twice with soap or cleansing cream.

Such daily skin care will dean and whiten the skin.

The following is the procedure for removing skin wastes and blemishes through the use of the cosmetic device of the present invention.

Figure 6A:
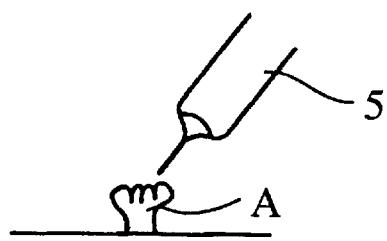
FIGS. 6(a) and (b) are diagrams for explaining how to remove a mole and a wart by the use of the cosmetic device according to the present invention.
Figure 6B:
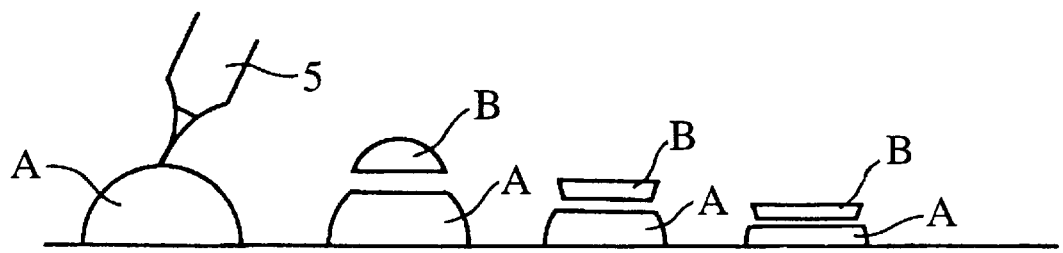

1. Hold the light beam probe 3 for 30 seconds to 1 minute against the skin wastes or blemishes to dull pain. The output intensity of the beam from the light beam probe 3 is adjusted by turning the beam output intensity adjustment knob 59. The ratio between the beam ON and OFF periods is adjusted by turning the ON and OFF time adjustment knobs 32 and 33, respectively.
2. Select either the needle or spherical pulse probe by the select switch 63.
3. Hold the needle pulse probe 5 against the skin wastes or blemishes for an appropriate length of time, depending upon whether the skin wastes or blemishes are large or small. For example, in the case of removing a small wart or mole A as shown in FIG. 6(A), hold the needle tip of the needle pulse probe 5 against the wart or mole A at the center thereof to irradiate its entire surface area with pulses from the needle tip. As a result, the wart or mole dries white and new skin forms under it. A large wart or mole can be removed by repeating the above procedure of FIG. 6(a) for several days. After several days, the surface of the wart or mole, becomes black and gradually comes off like a scab as depicted in FIG. 6(b).
4. After the removal of the skin wastes or blemishes, hold the needle pulse probe 5 to the skin to bleach or whiten and sterilize the skin surface concerned.
5. Apply appropriate cosmetics (preferably, additive-free) to face to protect the skin.

Blemishes on the back or hands can be removed by the same method as in the case of removing the blemishes from the face. In this case, it is important that the blemishes be irradiated uniformly all over them with ozone. After several days, the blemishes whiten because of evaporation therefrom of water, become dirt or scab-like and can easily be removed.

EFFECT OF THE INVENTION

The cosmetic device according to the present invention has such advantages as listed below.

1. Since skin wastes and blemishes can be decomposed, the skin can be cleaned.

2. Since sebaceous and sweat glands are activated, pimples, eruptions, blotches, moles, warts, hemorrhoids or similar skin blemishes can easily be eliminated from the skin surface at home.

It will be apparent that many modifications and variations may be effected without departing from the scope of the novel concepts of the present invention.

What is claimed is:

1. A cosmetic device comprising:
   a light beam generating part;
   a light beam probe for outputting therethrough a light beam from said light beam generating part;
   a high-potential pulse generating part;
   at least one pulse probe coupled to said high-potential pulse generating part for outputting therethrough high-potential pulses from said high-potential pulse generating part;
   a control part for controlling the intensity, output time and output interval of each light beam outputted from said light beam probe and said high-potential pulses outputted from said at least one pulse probe; and
   a display part for displaying a state of control by said control part and a state of operation of said cosmetic device.

2. The cosmetic device of claim 1, wherein said light beam probe comprises a halogen lamp.

3. The cosmetic device of claim 1, wherein said at least one pulse probe comprises at least one of a needle pulse probe and a spherical pulse probe.

4. The cosmetic device of claim 3, wherein said at least one pulse probe comprises a needle pulse probe.

5. The cosmetic device of claim 4, wherein said needle pulse probe comprises a discharge electrode, and wherein said needle pulse probe is arranged to discharge when said discharge electrode is placed adjacent the skin of a patient.

6. The cosmetic device of claim 5, wherein said needle pulse probe is arranged to discharge when said discharge electrode is placed one centimeter or less from the skin of the patient.

7. The cosmetic device of claim 3, wherein said at least one pulse probe comprises a spherical pulse probe.

8. The cosmetic device of claim 7, wherein said spherical pulse probe comprises a gas-filled lamp.

9. The cosmetic device of claim 8, wherein said gas-filled lamp has a discharge gas contained therein such that when a high frequency voltage is applied thereto, the discharge gas ionizes and discharges, thereby emitting light.

10. The cosmetic device of claim 9, wherein:
    said gas-filled lamp comprises a rounded glass member; and
    said spherical pulse probe causes electrical charges to flow to the skin of a patient from said gas-filled lamp when said rounded glass member is held in contact with the skin of the patient.

* * * * *